United States Patent [19]
Schroeppel et al.

[11] Patent Number: 5,749,909
[45] Date of Patent: May 12, 1998

[54] TRANSCUTANEOUS ENERGY COUPLING USING PIEZOELECTRIC DEVICE

[75] Inventors: Edward A. Schroeppel; Paul R. Spehr, both of Lake Jackson, Tex.

[73] Assignee: Sulzer Intermedics Inc., Angleton, Tex.

[21] Appl. No.: 746,220

[22] Filed: Nov. 7, 1996

[51] Int. Cl.⁶ .................................................... A61N 1/378
[52] U.S. Cl. ................................................. 607/33; 607/61
[58] Field of Search ................................. 607/33, 35, 61

[56] References Cited

U.S. PATENT DOCUMENTS

| | | | |
|---|---|---|---|
| 3,456,134 | 7/1969 | Ko | 607/35 |
| 3,563,245 | 2/1971 | McLean . | |
| 3,659,615 | 5/1972 | Enger | 607/35 |
| 3,824,129 | 7/1974 | Fagan, Jr. . | |
| 3,825,016 | 7/1974 | Lale et al. | 607/29 |
| 3,867,950 | 2/1975 | Fischell . | |
| 3,888,260 | 6/1975 | Fischell . | |
| 3,942,535 | 3/1976 | Schulman . | |
| 4,014,346 | 3/1977 | Brownlee et al. . | |
| 4,082,097 | 4/1978 | Mann et al. . | |
| 4,096,866 | 6/1978 | Fischell . | |
| 4,134,408 | 1/1979 | Brownlee et al. . | |
| 4,275,739 | 6/1981 | Fischell . | |
| 4,428,378 | 1/1984 | Anderson et al. . | |
| 4,432,363 | 2/1984 | Kakegawa . | |
| 4,614,192 | 9/1986 | Imran et al. . | |
| 4,651,740 | 3/1987 | Schroeppel | 607/30 |
| 4,661,107 | 4/1987 | Fink | 623/2 |
| 4,665,896 | 5/1987 | LaForge et al. . | |
| 4,690,143 | 9/1987 | Schroeppel . | |
| 4,941,472 | 7/1990 | Moden et al. . | |
| 5,205,286 | 4/1993 | Soukup et al. | 128/630 |
| 5,279,292 | 1/1994 | Baumann et al. | 607/137 |
| 5,411,537 | 5/1995 | Munshi et al. | 607/33 |

OTHER PUBLICATIONS

Encyclopedia of Electronic Circuits vol. 4; pp. 137, 351–352, 408–409.

*Primary Examiner*—Jeffrey R. Jastrzab
*Attorney, Agent, or Firm*—John R. Merkling; Conley, Rose & Tayon

[57] ABSTRACT

An energy transmission system for transmitting energy non-invasively from an external unit to an implanted medical device to recharge a battery in the medical device. An alternating magnetic field is generated by the external charging unit and a piezoelectric device in the implanted medical device vibrates in response to the magnetic flux to generate a voltage. The voltage is rectified and regulated to provide charging current to a rechargeable battery in the medical device. A series of piezoelectric devices may be connected in series to produce a larger voltage than can be produced by any one piezoelectric device. Acoustic waves generated by the external charging unit alternatively can be used to vibrate the piezoelectric device instead of a changing magnetic flux. The acoustic waves are generated by an external source coupled to a piezoelectric transducer.

19 Claims, 3 Drawing Sheets

TRANSCUTANEOUS ENERGY COUPLING USING PIEZOELECTRIC DEVICE

BACKGROUND OF THE INVENTION

1. Field of the Invention

The present invention relates generally to implantable medical devices. More particularly, the invention relates to battery-powered implantable medical devices that receive energy for recharging the battery from an external source. Still more particularly, the invention relates to a system and apparatus for transcutaneously recharging a battery in an implanted medical device.

2. Description of the Related Art

Many implantable medical devices, such as defibrillators and pacemakers, require an electrical energy source. In pacemakers and defibrillators, this energy source normally is provided by a battery pack that is contained within the implanted device. Although rechargeable batteries have been successfully employed in a variety of applications, most present day pacemakers and defibrillators use non-rechargeable batteries that are based on lithium iodine chemistries. Lithium iodine batteries are characterized by a high energy density and thus can provide a substantial amount of electrical power from a relatively small battery.

Surgery, with its attendant risks, discomforts, and cost is required when it becomes necessary to replace an implanted medical device. Because the batteries are hermetically sealed within the implanted device, the entire medical device must be surgically replaced if the batteries become depleted. To avoid or postpone surgery, it thus would be beneficial to provide longer lasting implantable devices. Longer life for an implant can be achieved by using a larger battery and/or reducing the power draw of the implant's circuitry. Using larger batteries undesirably increases the size of the implant's package. Reducing the power draw generally forces the elimination of various features that, although desirable, are less important than other features. Further, advances in pacemaker and defibrillator technology and medical protocols are so rapid that proper cardiac treatment for the patient may favor replacing the old implant with a newer better device. Replacement also may be necessary to address the changing needs of the patient's medical condition. Accordingly, the advantages of lithium iodine-based batteries coupled with other considerations, has encouraged the implant industry in recent years to provide pacemakers and defibrillators that employ non-rechargeable batteries.

Despite the prominence of non-rechargeable batteries for powering implanted medical devices, some situations favor the use of rechargeable batteries. Some implanted medical devices, such as ventricular assist devices, require large amounts of electrical power to operate. Such devices often are powered by an external, non-implanted power source with direct electrical connection through the skin to the implant or indirectly via induction coils. It is often desirable, however, to detach the external power source from the implant, for example, when the patient bathes. During the time that the external power source is detached, the implanted device operates from battery power. Because of the large energy demand of some such implanted devices, it would be desirable to provide a rechargeable battery source for the implant to avoid having to surgically intervene to replace the non-rechargeable batteries once they become depleted. Upon reconnecting the external power source, the internal rechargeable battery pack could be recharged.

It may also be desirable to add additional features to an implantable device's capabilities. Additional features, however, generally require additional power shortening the life of a non-rechargeable battery, thus highlighting the advantage of a rechargeable battery. If rechargeable batteries were used, features could be added that might not be possible with non-rechargeable batteries.

The cost of medical care in the United States has been the subject of intense national debate recently. Thus, even for medical devices in which advances in medical device technology might favor replacing the device before the battery pack is fully depleted, it is desirable not to replace the implanted medical device as frequently. Such a practice, however, necessitates either the use of rechargeable batteries, larger non-rechargeable batteries, or fewer features. The disadvantages of larger batteries and fewer features are discussed above.

Early rechargeable batteries suffered from a characteristic often referred to as the "memory effect." The memory effect describes the condition of reduced capacity that certain types of rechargeable batteries (e.g., nickel cadmium) experience after repetitively recharging the battery before the full capacity of the battery is used. A nickel cadmium battery's full capacity may not be available if the battery is continuously recharged before using the full capacity of the battery. Today, however, new rechargeable battery chemistries including lithium ion batteries do not suffer from the memory effect that has plagued nickel cadmium batteries. Lithium ion batteries, therefore, provide an attractive alternative to non-rechargeable batteries, at least in some situations.

In applications in which rechargeable batteries are employed, a system to recharge the batteries is necessary. Such a recharging system should be non-invasive or minimally invasive. Several recharging techniques have been attempted.

One technique for recharging an implanted device's battery involves transcutaneous energy transmission, a technique which allows non-invasive battery charging. Using transcutaneous energy transmission, such as described in U.S. Pat. No. 5,411,537, an alternating current (AC) in an external primary coil of wire creates a magnetic field which, in turn, induces an AC electrical current in a secondary coil of wire that is housed within the implanted medical device. Charging energy is thus transmitted in the same manner as between the primary and secondary coils of a transformer. The alternating current induced in the implanted secondary coil is then rectified and regulated to provide direct current (DC) power for charging the medical device's battery. This technique advantageously recharges the battery non-invasively.

Transcutaneous energy transmission, although generally safe and reliable, is not without certain shortcomings. For example, the efficiency of transcutaneously inducing a current in the implanted coil is detrimentally affected if the internal and external coils are not properly aligned or oriented, or if the distance between the external and internal coils is too great. Because there is no direct physical connection between the external charger and the implanted device to provide feedback, ascertaining whether transmission efficiency is maximized or whether the battery has become fully charged is problematic.

Also, as mentioned previously, transcutaneous energy transmission relies upon a magnetic field to induce an AC current in the implanted coil. At the same time, the alternating magnetic flux generated by the AC current induces the formation of eddy currents in the medical device's metal housing and in the metal casings of various components internal to the implantable device. The magnitude of these eddy currents is a function of the frequency and magnitude of the magnetic flux. Eddy currents cause a temperature increase in the metal components in which the current is conducted. If too great, the temperature increase in the implanted device caused by eddy currents can damage the surrounding body tissues. A high charging current, moreover, creates large temperature rises, thereby increasing the risk of harm to surrounding tissues.

To minimize patient discomfort, it is desirable that the implanted device and all its components be as small as possible. Unfortunately, because of the inefficiency associated with electromagnetic induction, it has been necessary to employ relatively large coils in conventional transcutaneous energy transmission schemes. A relatively large size for the internal coil causes the implanted medical device to be significantly larger than the device would otherwise need to be, and thus is not consistent with the design goal of producing smaller and lighter implantable devices.

A coil of wire generally acts as an antenna that is sensitive to electromagnetic radiation. The internal coil may thus act as an antenna potentially allowing undesirable electromagnetic interference to enter the implanted medical device. Such undesirable electromagnetic interference may compromise the correct functionality of the circuitry in the implanted device.

Another known recharging technique uses direct electrical connections between an external power source and an implanted receptacle. For example, U.S. Pat. No. 4,941,472 (Moden, et al) describes an implanted electrical access port to provide a receptacle for receiving needle electrodes. The electrical access port in Moden is electrically interconnected to an implanted medical device. L-shaped needle electrodes of Moden are inserted through the patient's skin and body tissue and inserted into opposite ends of the access port. Similarly, U.S. Pat. No. 5,205,286 (Soukup, et al) discloses a subcutaneous data port that provides a plurality of conductive ports for receiving needle electrodes. Multiple needle sticks are required with the Soukup device in order to mate the needles with all of the conductive ports, thus potentially increasing discomfort to the patient. Soukup and Moden also contemplate implanting the needle-receiving access port remotely from the implanted therapeutic device such that incisions in at least two locations are required.

Thus, there remains a need in the art for a system and apparatus to recharge batteries in an implanted medical device that overcomes these and other problems associated with such conventional systems. In particular, it would be desirable to provide an energy transmission system that can efficiently and non-invasively recharge a battery in an implanted medical device without heating the medical device and possibly damaging surrounding body tissues. It would be further advantageous to provide an energy transmission system that minimizes the size of components internal to the implanted device necessary for recharging the battery, and thus minimizes the overall size of the implanted device. Such a system should cause little, if any, discomfort or risk to the patient. Despite the substantial advantages that would be afforded by such a system, to date no such system has been developed.

SUMMARY OF THE INVENTION

An energy transmission system is provided for transmitting energy non-invasively from an external charging unit to an implanted medical device to recharge a battery in the medical device. An alternating magnetic field is generated by the external unit. One or more piezoelectric devices in the implanted medical device vibrate in response to the magnetic flux, thereby generating an AC voltage. The voltage is rectified and regulated to provide charging current to a rechargeable battery in the medical device. An alignment indicator is provided to ascertain the optimal orientation between the external unit and the implanted medical device. The piezoelectric devices are relatively small and thin and thus reduce packaging limitation problems caused by coils of wire used in conventional transcutaneous energy transmission systems.

Two or more piezoelectric devices may be connected in series in the implanted medical device to produce a voltage that is larger than that produced by any one piezoelectric device. A series connected combination of piezoelectric devices may be preferred to a single larger piezoelectric device because of packaging limitations regarding the implanted medical device and lack of availability of the larger piezoelectric devices.

In an alternative embodiment, instead of vibrating the piezoelectric device with a changing magnetic flux, sonic or ultrasonic vibrations are generated by an external acoustic source and are used to vibrate the implanted piezoelectric device. Preferably, the waves are generated by an external speaker such as another piezoelectric device. By driving the piezoelectric device by means other than an alternating magnetic field, undesirable heating of the implanted device and surrounding tissue are avoided.

Thus, the present invention comprises a combination of features and advantages which enable it to substantially advance the art associated with recharging batteries in implantable medical devices by providing a system and apparatus that non-invasively charges internal batteries and that employs using smaller and lighter components, thus increasing patient comfort. The invention requires no surgical intervention or needle penetrations of the patient's skin to recharge the batteries, and may be designed such that heating of the implanted medical device during charging is minimized. These and various other characteristics and advantages of the present invention will be readily apparent to those skilled in the art upon reading the following detailed description of the preferred embodiments of the invention, and by referring to the accompanying drawings.

BRIEF DESCRIPTION OF THE DRAWINGS

For a detailed description of the preferred embodiments of the invention, reference will now be made to the accompanying drawings wherein.

DETAILED DESCRIPTION OF THE PREFERRED EMBODIMENTS

Figure 1:
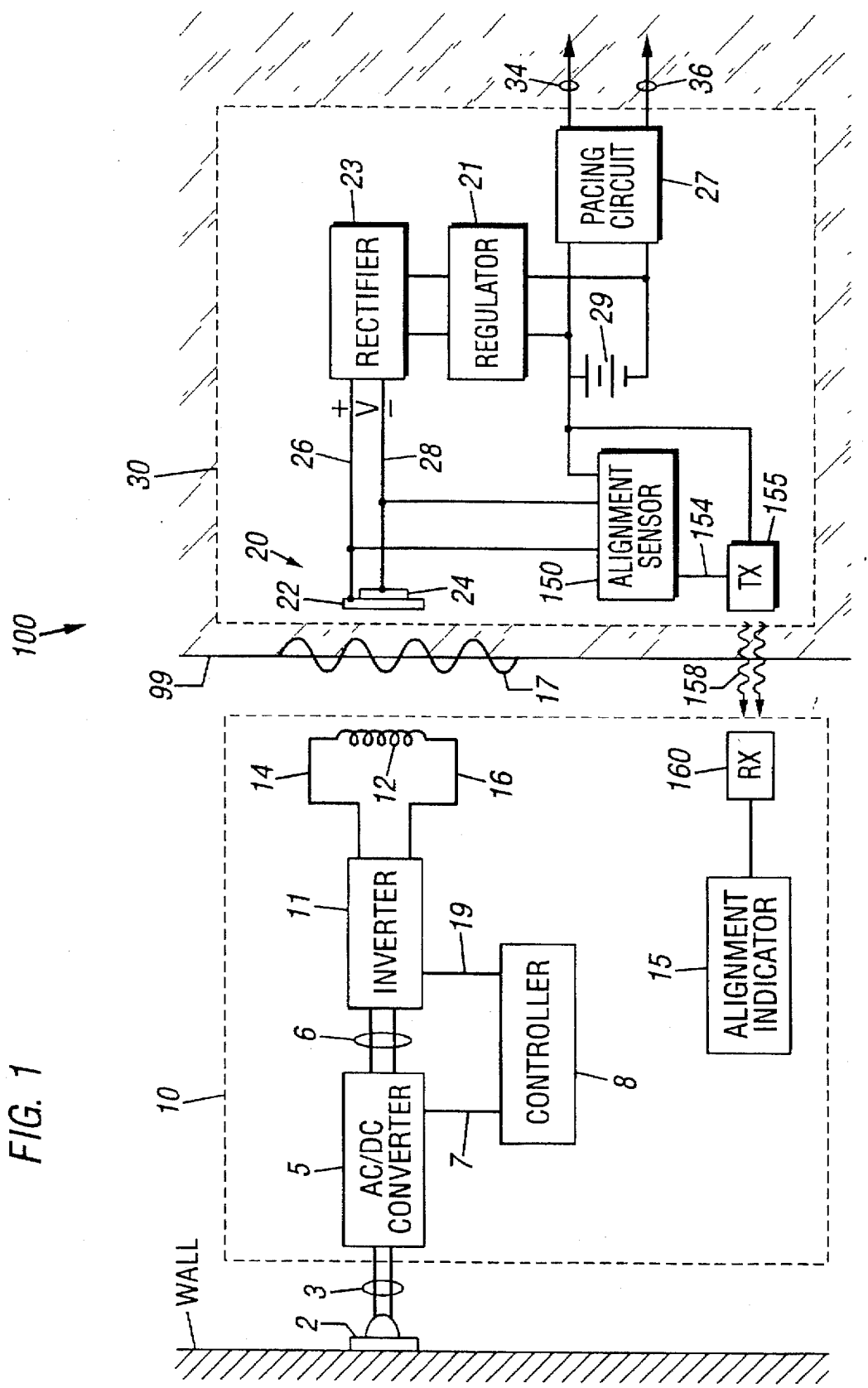
FIG. 1 is a schematic representation of the system of the present invention including an external charging unit with an alignment indicator for exciting a piezoelectric device in an implanted medical device.

Referring now to FIG. 1, a recharging system 100 consistent with a preferred embodiment of the present invention is shown to comprise an external charging unit 10 and an implanted medical device 30. Implantable medical device 30 may be any bioimplantable device such as a cardiac pacemaker, defibrillator, or drug infusion and dispensing system, as examples. For purposes of describing the preferred embodiments of the invention, it will hereafter be described as employed in a pacemaker. However, it should be understood that the invention may likewise be employed in any of a variety of implantable medical devices.

The external charging unit 10 includes a conventional alternating current-to-direct current (AC/DC) converter 5 which receives 120 VAC electrical power from a wall outlet 2 over conductors 3 or from some other conventional power source. AC/DC converter 5 converts the 120 VAC power received from wall outlet 2 to a lower magnitude DC voltage level. Inverter 11 receives the DC voltage from AC/DC converter 5 over conductors 6 and generates an AC current through coil 12 via conductors 14 and 16. Controller 8 receives operating power over conductor 7 from the AC/DC converter 5 and controls the operation of inverter 11 via control line 19. Controller 8 preferably controls the magnitude of current produced by the inverter 11 and may, if desired, cause inverter 11 to turn off current completely to coil 12 when the charging cycle is complete or when it is otherwise desirable to cease charging. Coil 12 may be housed within external unit 10 or housed separately. Coil 12 generates a magnetic field 17 which is received by implanted medical device 30 as described more fully below. Alignment indicator 15 receives a signal from a receiver (RX) 160 and, in response, provides a visual or audible indication of whether external charging unit 10 is properly positioned on the patient's skin 99 with respect to the implanted device 30.

Implanted medical device 30 preferably includes a piezoelectric device 20 connected to a rectifier 23. Piezoelectric device 20 generates electrical power to charge the medical device's battery 29. Piezoelectric device 20 includes a ferromagnetic plate 22 bonded by means of epoxy to a ceramic disk 24. Conductors 26 and 28 couple ferromagnetic plate 22 and ceramic disk 24, respectively, to rectifier 23. Rectifier 23 connects to a rechargeable battery 29 via a voltage regulator 21. Battery 29 provides the electrical energy needed to power the pacing circuitry 27 of implantable medical device 30 and other internal components, including alignment sensor 150 and transmitter (TX) 155. Alignment sensor 150 also connects to conductors 26 and 28. Alignment sensor 150 provides a signal 154 to TX 155. As explained below, the signal 154 preferably indicates how closely the external unit 10 is to an optimal location on the patient's skin 99. In response to signal 154, TX 155 transmits a signal 158 across the skin 99 to the RX 160 in the external unit 10 and alignment indicator 15.

As one of ordinary skill in the art will recognize, an alternating current through coil 12 generates the changing magnetic field 17 which causes ferromagnetic plate 22, and piezoelectric ceramic disk 24 to vibrate. The frequency and magnitude of the mechanical vibrations of piezoelectric device 20 are proportional to the magnitude and frequency of the magnetic field 17. An AC voltage V across conductors 26 and 28, results from the mechanical vibrations of the piezoelectric device 20. Thus, the magnitude and frequency of voltage V is a function of the magnitude and frequency of magnetic field 17. The voltage V generated by the piezoelectric device 20 is converted to an appropriate DC level for battery charging by voltage rectifier 23 and voltage regulator 21. Rectifier 23 converts the AC voltage V from piezoelectric device 20 to a DC level, and regulator 21 maintains the DC voltage at a desired level under varying load conditions. Any commonly known rectifier and regulator circuits are consistent with the preferred embodiment. Regulated power from regulator 21 charges battery 29. In sum, an alternating current is driven through external coil 12 to generate changing magnetic field 17 which, in turn, causes piezoelectric device 20 to generate a voltage V. Voltage V is then used to recharge the implanted medical device's battery.

The efficiency through which coil 12 can force piezoelectric device 20 to vibrate depends, at least in part, on the physical placement of external coil 12 relative to the piezoelectric device of the implanted medical device. For maximum energy efficiency, coil 12, and charging circuit 10 (if coil 12 is housed within charging circuit 10), should be positioned such that the maximum number of lines of magnetic flux of magnetic field 17 cross the surface of the ferromagnetic plate 22. Generally, optimal placement requires coil 12 to be positioned on the skin directly over the site at which the implanted device 30 is located (optimal site). The magnitude of the voltage V generated by the piezoelectric device 20 diminishes as coil 12 is moved away from the optimal site; the farther away coil 12 is moved, the smaller voltage V becomes. Alignment sensor 150 preferably includes a commonly known voltage sensor and provides an output signal along conductor 154 representative of voltage V. As coil 12 is moved along the patient's skin toward the site directly over the implanted device 30, the magnitude of voltage V increases and as coil 12 is moved away from the optimal site, voltage V decreases. Using commonly known encoding techniques, the signal transmitted along conductor 154 is representative of voltage V.

TX 155 telemeters the information represented by the signal on conductor 154 to the RX 160 in external unit 10. TX 155 and RX 160 comprise a typical telemetry system such as is found in many commonly known implantable devices. Alignment indicator 15 receives the transmitted information from RX 160 and indicates the information visually or audibly to a physician or technician. The information indicated may thus be the voltage V or a tone whose pitch increases as coil 12 approaches the optimal site, or the like. Coil 12 (or external unit 10 if coil 12 is housed within external unit 10) is placed at different locations on skin 99 until alignment indicator 15 indicates the coil is at optimal site.

For implanted devices which do not include a telemetry system such as that described above, an alignment system using a metal detector, such as the medical detectors disclosed on pages 137, 351-352, and 408-409 of *Encyclopedia of Electronic Circuits* (Rudolf Graf and William Sheets, Publisher: TAB Books, a division of McGraw-Hill, Inc., copyright, 1992) can be used. Pages 137, 351-352, and 408-409 of *Encyclopedia of Electronic Circuits* are incorporated by reference. A metal detector-based alignment system will detect the location of the medical device's metal housing.

Figure 2A:
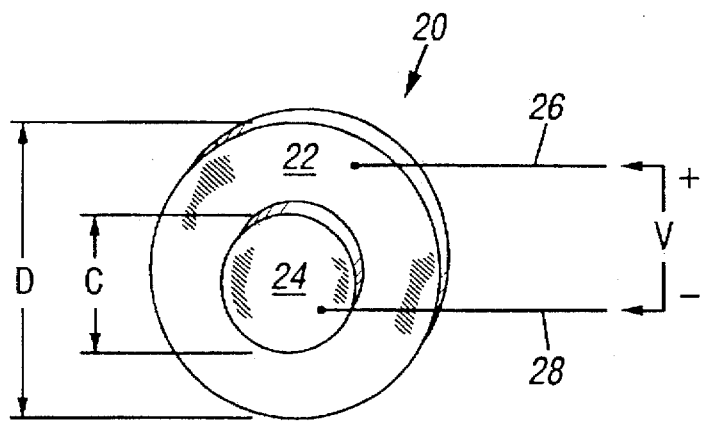
FIG. 2A is a perspective view of the implanted piezoelectric device of the present invention.
Figure 2B:
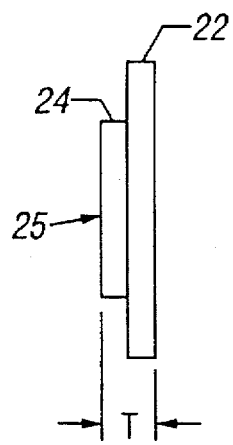
FIG. 2B is a side view of the piezoelectric device of FIG. 2A.

Referring now to FIGS. 2A and 2B, the piezoelectric device 20 of FIG. 1 includes a piezoelectric ceramic disk 24 bonded to a ferromagnetic plate 22 using commonly known bonding techniques. A metal coating (not shown) coats the surface 25 of ceramic disk 24 providing a conductive surface to which conductor 28 may be attached. Conductors 28 and 26 (FIG. 2A) are bonded on to the ferromagnetic plate 22 and to the metal coating of the piezoelectric ceramic disk 24 preferably using conductive epoxy cement. Preferably, the ferromagnetic plate 22 is made of brass and has a diameter D of 50 millimeters. The ceramic disk 24 preferably has a diameter C of 30 millimeters. The thickness T (FIG. 2B) of the piezoelectric device 20 preferably is 0.15 millimeters. The piezoelectric device 20 also preferably has a resonant frequency in the range of 0.5 to 1.5 KHz. The resonant frequency generally is the frequency at which the device is vibrated to produce maximum voltage across conductors 26 and 28. Although Panasonic piezoelectric devices EFB-S15A01, EFB-S11A05, and EFB-S07A03 are preferred, a variety of piezoelectric devices with different specifications can be used in the present invention. As one of ordinary skill in the art will recognize, the dimensions of the piezoelectric device depend on the size of the implanted medical device.

Figure 6:
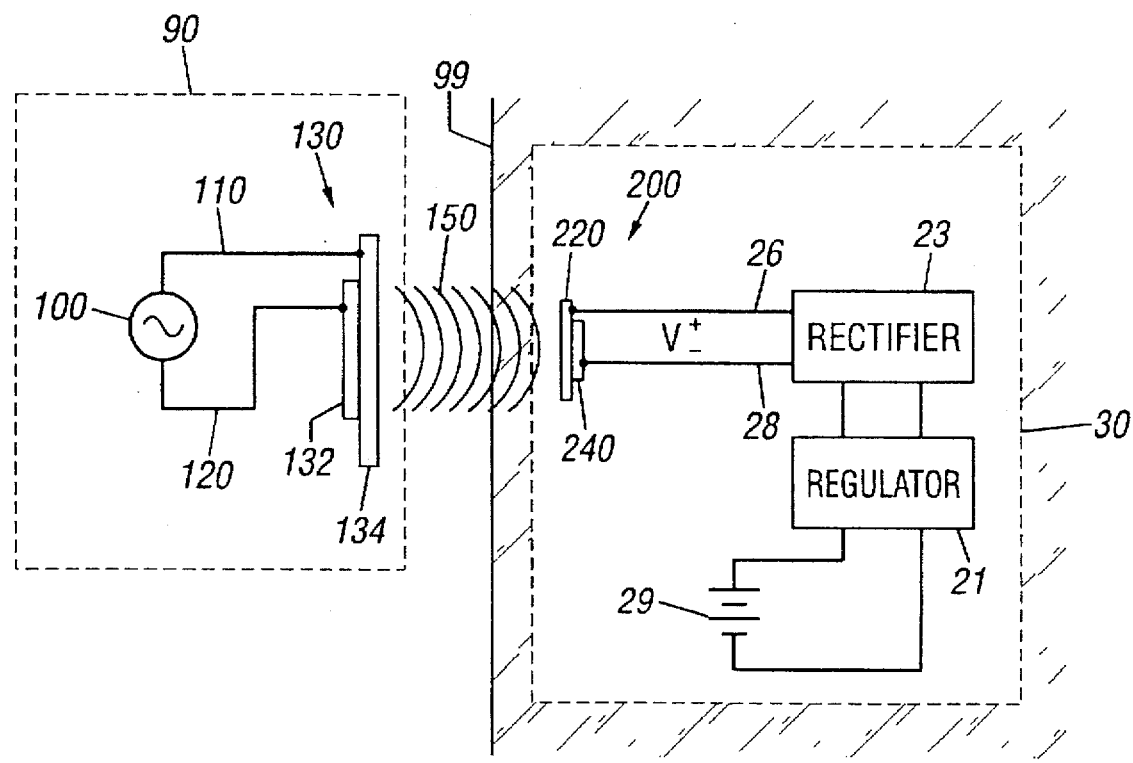
FIG. 6 is a schematic representation of an alternative embodiment of the present invention including an external charging unit for generating acoustic waves to excite a piezoelectric device in an implanted medical device.

As discussed above, the AC voltage represented by the letter V (FIG. 2A) is produced between ferromagnetic plate 22 and piezoelectric ceramic disk 24 (and thus between conductors 26 and 28) in response to vibrations experienced by the combination of the ferromagnetic plate 22 and piezoelectric ceramic disk 24. External forces vibrate the piezoelectric device 20 causing the device 20 to generate the voltage V. Although the embodiment of FIG. 1 discloses a magnetic field for vibrating piezoelectric device 20, other sources of vibrations are possible such as acoustic waves as shown in FIG. 6. Vibrations preferably are caused by a changing magnetic field or sound waves and the present invention encompasses both sources. One of ordinary skill in the art will recognize other techniques for vibrating an implanted piezoelectric device, and the present invention is intended to include those other techniques as well.

Figure 3:
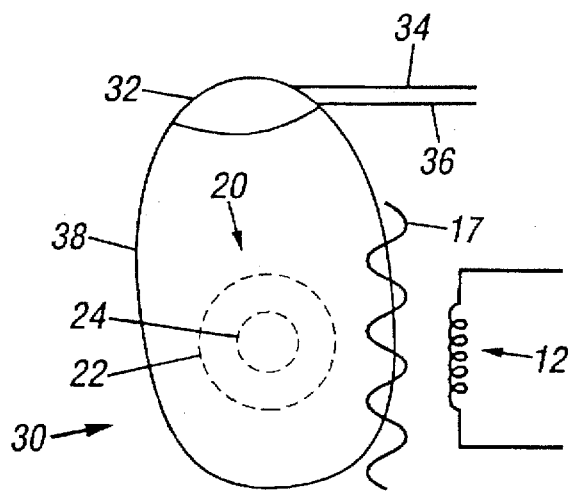
FIG. 3 is a front elevational view of the implantable medical device of FIG. 1 housing a single piezoelectric device.

Referring now to FIG. 3, an implanted pacemaker 30 is shown, although the present invention is applicable to almost any implantable medical device operating from rechargeable batteries including ventricular assist devices, defibrillators, drug delivery systems and other devices. The pacemaker 30 supplies electrical pulses of predetermined duration and magnitude to remotely implanted electrodes (not shown) via conductors 34, 46. The implanted medical device 30 includes housing 38 and header 32. Housing 38 contains the electrical components comprising the medical device 30 including rechargeable batteries 29 and pulse generation circuitry 27. Housing 38 also includes a piezoelectric device 20 consisting of piezoelectric ceramic disk 24 bonded to ferromagnetic plate 22. Header 32 serves as a coupling mechanism for connecting leads 34 and 38 to electronic circuits within housing 38. Leads 34 and 36 pass through header 32 and are connected to pulse generation circuitry 27 in housing 38. The openings in header 32 through which leads 34, 36 pass are sealed by header 32 to prevent body fluids from entering housing 38 and damaging the internal circuitry and components. Magnetic field 17 generated by external unit 10 passes through housing 38 and impinges on piezoelectric device 20 causing it to vibrate as explained above.

Figure 4:
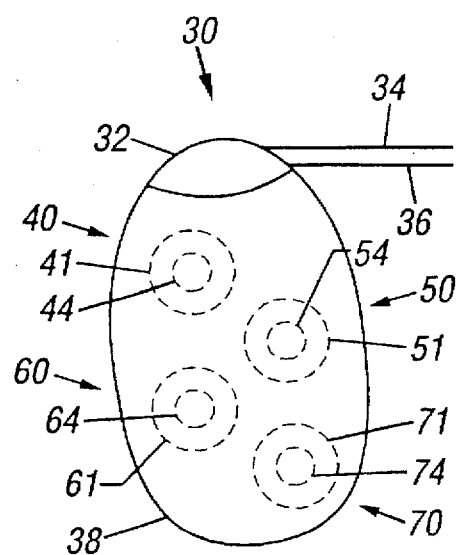
FIG. 4 is a front elevational view of an implanted medical device housing a plurality of piezoelectric devices.

Although the piezoelectric device 20 described in FIGS. 2A and 2B is relatively small, exacting packaging tolerances and space constraints within device 30 in some instances may make even a 50 millimeter diameter device undesirable. Therefore, it may desirable to use multiple smaller piezoelectric devices. FIG. 4, for example, shows an implanted medical device 30 containing four smaller piezoelectric devices 40, 50, 60, 70. As with the piezoelectric device 20 of FIG. 1, piezoelectric device 40 includes a piezoelectric ceramic disk 44 bonded to a ferromagnetic plate 41. Similarly, piezoelectric device 50 includes a ceramic disk 54 bonded to a ferromagnetic plate 51. Piezoelectric device 60 includes a ceramic disk 64 bonded to a ferromagnetic plate 61 and piezoelectric device 70 includes a ceramic disk 74 bonded to a ferromagnetic plate 71.

Figure 5:
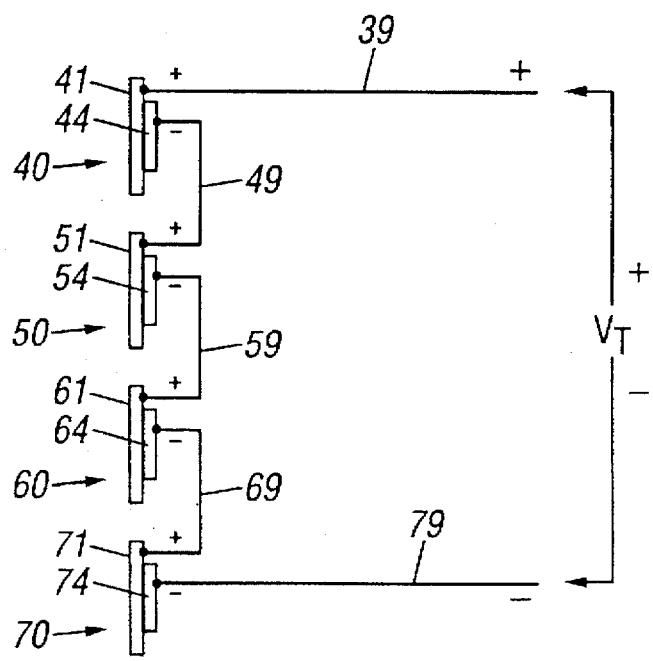
FIG. 5 is a schematic representation of the electrical interconnection of the plurality of piezoelectric devices of FIG. 4.

An advantage of this embodiment is demonstrated in FIG. 5. Piezoelectric devices 40, 50, 60, 70 are electrically interconnected in series through conductors 49, 59, 69. The negative terminal of each piezoelectric device (i.e. the ceramic disks) is electrically coupled to the ferromagnetic plate of an adjacent piezoelectric device. Preferably, ceramic disk 44 of piezoelectric device 40 connects through conductor 49 to ferromagnetic plate 51 of piezoelectric device 50. Further, ceramic disk 54 couples through conductor 59 to ferromagnetic plate 61 of piezoelectric device 60, and ceramic disk 64 couples through conductor 69 to the ferromagnetic plate 71 of piezoelectric device 70. Conductor 39 connects to the ferromagnetic plate 41 of piezoelectric device 40 providing a positive terminal or anode for the combination of piezoelectric devices 40, 50, 60, 70, and conductor 79 connects to the ceramic disk 74 of piezoelectric device 70 to provide a negative terminal or cathode of the piezoelectric device combination.

The voltages generated by each piezoelectric device 40, 50, 60, 70 are summed and the summation of voltages is represented by voltage $V_T$ across conductors 39 and 79. By serially connecting multiple piezoelectric devices, a greater voltage $V_T$ can be generated across the combination than is produced by any one sensor. Thus, in applications in which a larger diameter voltage piezoelectric device cannot be used because of packaging constraints, multiple smaller piezoelectric devices can be wired in series to produce a desirable voltage.

It is commonly known that piezoelectric devices can convert mechanical energy in the form of vibrations to electrical energy, and vice versa. In other words, not only can a piezoelectric device produce a voltage when physically vibrated, but it can be made to vibrate emitting an audible tone upon the application of an AC voltage. Thus, a piezoelectric device can act as an audio speaker or buzzer as well as an electrical energy source. Piezoelectric buzzers are commonly found in many products today. The present invention contemplates the use of piezoelectric devices in both capacities—as an electrical energy source as described above and as a speaker as described below.

Referring now to FIG. 6, an alternative embodiment is shown using acoustic waves rather than a magnetic field to excite an implanted piezoelectric device. External unit 90 includes an acoustic signal source 100 connected preferably to a speaker 130 through conductors 110 and 120. Speaker 130 preferably includes a piezoelectric transducer or any other acoustic source capable of emitting acoustic waves receivable by an implanted device. The frequency of the acoustic waves may be in the audible range or higher including, but not limited to, frequencies in the ultrasonic (frequencies generally higher than 20 KHz), sonar (generally 25–100 KHz), medical ultrasonic (generally 1–10 MHz), and microwave acoustic (frequencies generally over 50 MHz) ranges. The following discussion assumes a piezoelectric buzzer as speaker 130. Piezoelectric buzzer 130 includes a plate 134 and a ceramic disk 132. Conductor 110 connects to plate 134 and conductor 120 connects to ceramic disk 132. Piezoelectric buzzer 130 may be constructed in a manner substantially the same as piezoelectric device 20 previously described (FIG. 1), but plate 134 need not be ferromagnetic. As one of ordinary skill in the art will recognize, changing electrical signals from audio source 100 causes piezoelectric buzzer 130 to vibrate, thereby emitting sound waves 150. The frequency and amplitude of sound waves 150 are a function of the frequency and amplitude of the signals from audio source 100.

Piezoelectric device 200 in implanted device 30 includes a ferromagnetic plate 220 bonded to a ceramic disk 240 and is preferably of the same construction as piezoelectric devices described previously with reference to FIGS. 1, 2A and 2B. Conductors 26 and 28 are bonded to plate 220 and ceramic disk 240 which is coated with a thin conductive film. Sound waves 150 impinge on piezoelectric device 200 causing the plate 220 and piezoelectric ceramic disk 240 to vibrate, generating voltage V across conductors 26 and 28. Although not shown in FIG. 6, an alignment system as described in FIG. 1 preferably is incorporated into the implanted device 30 of the embodiment of FIG. 6.

While preferred embodiments of this invention have been shown and described, modifications thereof can be made by one skilled in the art without departing from the spirit or teaching of this invention. For example, piezoelectric devices 20, 40, 50, 60, 70, 200 may be provided external to the implanted medical device and located underneath the skin to provide increased transmission efficiency. The embodiments described herein are exemplary only and are not limiting. Many variations and modifications of the system and apparatus are possible and are within the scope of the invention. Accordingly, the scope of the protection is not limited to the embodiments described herein, but is only limited by the claims which follow, the scope of which shall include all equivalents of the subject matter of the claims.

We claim as our invention:

1. A cardiac stimulation system comprising: a cardiac stimulator having:

a hermetically sealed container, a cardiac stimulation circuit within said container for producing an output to stimulate the heart, an electrode coupled to said cardiac stimulation circuit for delivering said output to the heart, a rechargeable battery coupled to said cardiac stimulation circuit, a rectifier coupled to said battery, and a piezoelectric device coupled to said rectifier said piezoelectric device including a ferromagnetic plate and a ceramic disc, said piezoelectric device capable of responding to any of at least two different types of external stimuli, and an external charging unit having means for displacing said piezoelectric device to cause said piezoelectric device to vibrate.

2. The system according to claim 1 wherein said means for displacing comprises a coil; and an alternating current source coupled to said coil, wherein said coil receives an alternating current from said alternating current source and generates a changing magnetic field which causes said piezoelectric device to vibrate.

3. The system of claim 2, wherein the vibrations of said piezoelectric device cause said piezoelectric device to produce a voltage which is rectified by said rectifier and used to charge said battery.

4. The system according to claim 1 wherein said means for displacing comprises:

an external acoustic source;

an external speaker connected to said external acoustic source for generating acoustic waves in response to signals from said external acoustic source, and wherein said piezoelectric device is responsive to said acoustic waves.

5. The system of claim 4, wherein said speaker comprises a piezoelectric device.

6. An energy transmission system for providing energy to an implantable medical device, comprising:

an implantable piezoelectric device including a ferromagnetic plate and a ceramic disc;

an implantable rectifier coupled to said piezoelectric device;

an implantable battery coupled to said rectifier;

an external coil; and an external alternating current source coupled to said external coil, wherein said external coil receives an alternating current from said alternating current source and generates a changing magnetic field which causes said piezoelectric device to vibrate.

7. The system of claim 6 wherein the vibrations of said piezoelectric device cause said piezoelectric device to produce a voltage which is rectified by said implantable rectifier and used to charge said implantable battery.

8. An energy transmission system for an implantable device, comprising:

an external acoustic source;

an external speaker connected to said external acoustic source for generating an acoustic stimulus in response to signals from said external acoustic source;

an implantable energy receiver means for responding to both said acoustic waves generated by said external speaker and at least one other type of external stimulus;

an implantable rectifier coupled to said implantable energy receiver; and an implantable battery coupled to said rectifier.

9. The system of claim 8, wherein the implantable energy receiver comprises a piezoelectric device.

10. The system of claim 8, wherein said implantable energy receiver produces electrical energy in response to receiving said acoustic waves.

11. The system of claim 10, wherein said implantable rectifier rectifies said electrical energy produced by said implantable energy receiver for recharging said implantable battery.

12. The system of claim 11, wherein the implantable energy receiver comprises a piezoelectric device.

13. The system of claim 12, wherein said speaker comprises a piezoelectric device.

14. A system for transcutaneously recharging a battery in an implantable medical device comprising:

a sealed container for implanting in a patient;

a rechargeable battery in said container;

a piezoelectric device in said container electrically coupled to said battery for generating a voltage to recharge said battery said piezoelectric device including a ferromagnetic plate and a ceramic disc, said piezoelectric device responsive to at least two external stimuli, any of which causes said piezoelectric device to vibrate;

a charging unit external to said container for stimulating said piezoelectric device by causing said piezoelectric device to vibrate to generate said voltage.

15. The system according to claim 14 wherein said charging unit includes a coil conducting alternating current and generating a changing magnetic field that impinges on said piezoelectric device.

16. The system of claim 15 wherein said charging unit includes an acoustic source for generating acoustic waves that impinge on said piezoelectric device.

17. The system of claim 16 wherein said acoustic source comprises a speaker.

18. The system of claim 16 wherein said acoustic source comprises a second piezoelectric device.

19. The system of claim 14 further comprising a plurality of piezoelectric devices in said container electrically connected in a series configuration, said series configuration coupled to said battery for generating a voltage to recharge said battery, each of said plurality of piezoelectric devices being responsive to an external stimulus that causes said piezoelectric devices to vibrate.

* * * * *